(12) United States Patent
Jang et al.

(10) Patent No.: US 7,474,917 B2
(45) Date of Patent: Jan. 6, 2009

(54) MEASUREMENT SYSTEM AND ELECTRODE FOR MEASURING SKIN IMPEDANCE IN A SMALL REGION OF SKIN

(75) Inventors: Woo-young Jang, Seoul (KR); Young-bae Park, Seoul (KR); Sang-hoon Shin, Sungnam (KR); Jin-wook Choi, Seoul (KR)

(73) Assignee: Samsung Electronics Co., Ltd., Suwon, Kyungki-do (KR)

( * ) Notice: Subject to any disclaimer, the term of this patent is extended or adjusted under 35 U.S.C. 154(b) by 197 days.

(21) Appl. No.: 10/624,532

(22) Filed: Jul. 23, 2003

(65) Prior Publication Data
US 2004/0122336 A1 Jun. 24, 2004

(30) Foreign Application Priority Data
Jul. 25, 2002 (KR) ................. 10-2002-0043926

(51) Int. Cl.
*A61B 5/05* (2006.01)
*A61B 5/04* (2006.01)

(52) U.S. Cl. ..................... 600/547; 600/393
(58) Field of Classification Search ............ 600/372, 600/382, 384, 393, 506, 547, 554; 324/444, 324/446, 447, 692, 715, 724
See application file for complete search history.

(56) References Cited

U.S. PATENT DOCUMENTS

| | | | | |
|---|---|---|---|---|
| 3,784,908 A | * | 1/1974 | Anderson | 600/547 |
| 3,871,359 A | * | 3/1975 | Pacela | 600/547 |
| 3,957,037 A | | 5/1976 | Fletcher et al. | |
| 3,971,366 A | * | 7/1976 | Motoyama | 600/384 |
| 4,578,635 A | | 3/1986 | Mee et al. | |
| 4,895,163 A | * | 1/1990 | Libke et al. | 600/547 |
| 4,917,093 A | * | 4/1990 | Dufresne et al. | 607/62 |
| 5,114,424 A | * | 5/1992 | Hagen et al. | 606/32 |
| 5,246,008 A | | 9/1993 | Mueller | |
| 5,372,141 A | * | 12/1994 | Gallup et al. | 600/547 |
| 5,810,762 A | * | 9/1998 | Hofmann | 604/20 |
| 5,964,703 A | | 10/1999 | Goodman et al. | |

(Continued)

FOREIGN PATENT DOCUMENTS

EP    1 138 259 A2    10/2001

(Continued)

*Primary Examiner*—Max Hindenburg
*Assistant Examiner*—H. Q. Nguyen
(74) *Attorney, Agent, or Firm*—Lee & Morse, P.C.

(57) ABSTRACT

An impedance measurement system for measuring skin impedance in a small skin region includes an electrode unit having a plurality of current supply electrodes for supplying a constant current and a plurality of measurement electrodes separate from the current supply electrodes for measuring a response signal of skin, a current source for supplying the constant current to the current supply electrodes, a signal processing unit, connected to the measurement electrodes, for receiving response signals generated in the skin in response to the applied constant current, for generating a potential difference signal, for removing noise from the potential difference signal, and for amplifying the noise-removed potential difference signal, a signal conversion unit for converting the potential difference signal received from the signal processing unit from analog into digital format, and an image display unit for converting the digital potential difference signal into an image signal and for displaying the image signal.

41 Claims, 8 Drawing Sheets

U.S. PATENT DOCUMENTS

| | | | |
|---|---|---|---|
| 6,292,690 B1 * | 9/2001 | Petrucelli et al. | 600/547 |
| 6,408,204 B1 * | 6/2002 | Hirschman | 600/547 |
| 6,631,292 B1 * | 10/2003 | Liedtke | 600/547 |
| 2002/0040193 A1 | 4/2002 | Hirschman | |
| 2003/0070942 A1 | 4/2003 | Ossart | |
| 2003/0176808 A1 * | 9/2003 | Masuo | 600/547 |
| 2004/0133121 A1 * | 7/2004 | Ohkura | 600/547 |

FOREIGN PATENT DOCUMENTS

| | | |
|---|---|---|
| EP | 1 138 259 A3 | 10/2001 |
| KR | 1988-0004785 | 6/1988 |
| KR | 93-701946 | 9/1993 |
| WO | WO 00/19894 | 4/2000 |
| WO | WO 01/79828 A1 | 10/2001 |
| WO | WO 03/017834 A1 | 3/2003 |

* cited by examiner

MEASUREMENT SYSTEM AND ELECTRODE FOR MEASURING SKIN IMPEDANCE IN A SMALL REGION OF SKIN

BACKGROUND OF THE INVENTION

1. Field of the Invention

The present invention relates to a measurement system for measuring skin impedance (i.e., a resistance value) in a small region of the skin and an electrode used in the measurement system. More particularly, the present invention relates to an impedance measurement electrode separately provided with a current supply electrode and a measurement electrode for measuring skin impedance in a small region of the skin and an impedance measurement system using the same.

2. Description of the Related Art

Since the results of an analysis of skin impedance values in a small region of the skin are used in a variety of applications, a method and apparatus for accurately measuring skin impedance have been researched and developed. In general, conventional technology of measuring skin impedance is used to detect meridian points on the skin, which are used to diagnose a disease and treat the disease in the field of Chinese medicine.

A meridian point, which is used in Chinese medicine or hand therapy (such as acupuncture, moxibustion, and massage), is a reaction point in the skin or a muscle. A meridian system is a channel connecting multiple reaction points. In the view of Chinese medicine, and more particularly hand therapy, the human body includes internal organs (i.e., the five viscera and the six entrails). Under healthy conditions, the functions of these internal organs harmonize with one another. Under unhealthy conditions, the harmony among the functions of the internal organs is disrupted and symptoms of a certain disease may be present. An energy circulating system (in which vital energy and blood flows), which passes through the human body, inside and outside thereof, and controls the functions of the internal organs, is a meridian system.

Accordingly, it is critical to accurately locate the positions of the meridian points and the meridian system for diagnosis and treatment in Chinese medicine. The meridian points and the meridian system can be accurately located by measuring skin impedance based on the principle that regions corresponding to the meridian points and the meridian system have a lower electrical resistance than other skin regions.

In addition, it has been reported that by measuring the skin impedance it is possible to diagnose cutaneous cancer, determine the degree of a burn, detect motion, detect a capacity for rehabilitative exercise, and determine normality or abnormality of a lymph node in the skin. As such, it is expected that various techniques based on measuring skin impedance will be increasingly used.

However, most conventional methods of measuring skin impedance are performed on the whole body rather than in a small region of the body. Moreover, most conventional methods of measuring skin impedance either on the whole body or in a local region of the body use only two or three electrodes. In that conventional arrangement, at least one electrode serves as both a measurement electrode and an electrode applying voltage or current. Accordingly, in addition to real skin impedance obtained from the dermis and the subcutis, a contact resistance and an epidermis impedance are included in a measured value. Thus, it is impossible to accurately measure the skin impedance because of the contact resistance and epidermis impedance.

More particularly, the measured value of the contact resistance varies significantly with a measurer's skillfulness (for example, an ability to control the contact speed and the contact pressure of an electrode) and conditions of a skin surface contacting an electrode, e.g., temperature and humidity, thereby significantly affecting the measured value of skin impedance.

Accordingly, it is difficult to obtain an accurate measured value of skin impedance using conventional techniques.

SUMMARY OF THE INVENTION

A feature of an embodiment of the present invention is to provide an impedance measurement electrode separately provided with a current supply electrode and a measurement electrode for measuring skin impedance in a small region of the skin.

Another feature of an embodiment of the present invention is to provide an impedance measurement electrode in which a distance between a current supply electrode and a measurement electrode can be adjusted freely.

Still another feature of an embodiment of the present invention is to provide an impedance measurement system for accurately measuring skin impedance in a small range of the skin using an impedance measurement electrode in which a power supply terminal and a measurement terminal are separate from each other.

According to an aspect of the present invention, there is provided an impedance measurement system for measuring skin impedance in a small skin region, including an electrode unit having a plurality of current supply electrodes for supplying a constant current and a plurality of measurement electrodes separate from the current supply electrodes for measuring a response signal of skin, a current source for supplying the constant current to the current supply electrodes, a signal processing unit, which is connected to the measurement electrodes, for receiving response signals generated in the skin in response to the applied constant current, for generating a potential difference signal, for removing noise from the potential difference signal, and for amplifying the noise-removed potential difference signal, a signal conversion unit for converting the potential difference signal received from the signal processing unit from an analog format into a digital format, and an image display unit for converting the digital potential difference signal into an image signal and for displaying the image signal.

According to another aspect of the present invention, there is provided an impedance measurement electrode used to measure skin impedance in a small skin region, including a plurality of current supply electrodes for supplying a constant current to skin, and a plurality of measurement electrodes, which are separated from the current supply electrodes, for measuring a response signal of the skin, wherein the measuring electrodes are disposed between the current supply electrodes.

Preferably, the current supply electrodes include a first electrode having a cylindrical structure and a second electrode having a cylindrical structure surrounding and concentric with the first electrode, wherein the measurement electrodes include third and fourth electrodes disposed between the first and second electrodes, the third and fourth electrodes having a cylindrical structure surrounding and concentric with the first electrode.

Preferably, the current supply electrodes include a first electrode having a first side, a second side perpendicular to the first side, and a third side perpendicular to the second side and facing the first side, and a second electrode having a same shape as the first electrode, the second electrode being disposed separate from the first electrode such that an opening side of the second electrode faces an opening side of the first electrode, wherein the measurement electrodes are disposed in an inner space defined between the first and second electrodes. Also preferably, the measurement electrodes are disposed perpendicular to the first and second electrodes.

Preferably, the measurement electrodes include a third electrode having a first side, a second side perpendicular to the first side, and a third side perpendicular to the second side and facing the first side, and a fourth electrode having a same shape as the third electrode, the fourth electrode being disposed separate from the third electrode such that an opening side of the fourth electrode faces an opening side of the third electrode, wherein the third and fourth electrodes are disposed between the plurality of current supply electrodes. Also preferably, the third and fourth electrodes are disposed perpendicular to the plurality of current supply electrodes.

Preferably, the current supply electrodes include a first electrode having an oval structure with an opening portion and a predetermined curvature, and a second electrode having a same shape as the first electrode, the second electrode being disposed separate from the first electrode such that an opening of the second electrode faces an opening of the first electrode, wherein the measurement electrodes are disposed in an inner space defined between the first and second electrodes. Also preferably, the measurement electrodes are disposed perpendicular to the first and second electrodes.

Preferably, the measurement electrodes include a third electrode having an oval structure with an opening portion and a predetermined curvature, and a fourth electrode having a same shape as the third electrode, the fourth electrode being disposed separate from the third electrode such that an opening of the fourth electrode faces an opening of the third electrode, wherein the third and fourth electrodes are disposed between the plurality of current supply electrodes. Also preferably, the third and fourth electrodes are disposed perpendicular to the plurality of current supply electrodes.

Preferably, the current supply electrodes have a flat structure, the measurement electrodes have a flat structure, the current supply electrodes and the measurement electrodes are disposed parallel to each other, and the measurement electrodes are disposed between the current supply electrodes.

Preferably, the electrode unit includes a first electrode distance adjuster for adjusting a distance between the current supply electrodes including a first stationary screw line connected to the current supply electrodes, a first rotary screw joined to the first stationary screw line and rotating the first stationary screw line to move the current supply electrodes along the first stationary screw line, and a fixing stud for fixing each of the current supply electrodes to the first stationary screw line; and a second electrode distance adjuster for adjusting a distance between the measurement electrodes including a second stationary screw line connected to the measurement electrodes, a second rotary screw joined to the second stationary screw line and rotating the second stationary screw line to move the measurement electrodes along the second stationary screw line, and a fixing stud for fixing each of the measurement electrodes to the second stationary screw line, wherein the first stationary screw line and the second stationary screw line are separated from each other by a predetermined distance and are perpendicular to each other.

Preferably, the electrode unit includes a stationary screw line connected to the current supply electrodes and the measurement electrodes, a rotary screw, which is joined to the stationary screw line, for rotating the stationary screw line to move the current supply electrodes and the measurement electrodes along the stationary screw line, and a fixing stud for fixing each of the current supply electrodes and the measurement electrodes to the stationary screw line.

Preferably, the current source includes an input unit for dividing a voltage received from an external power supply unit into predetermined voltages and for outputting the predetermined voltages, a current converter for converting each of the predetermined voltages into a constant current regardless of a load, a current intensity controller for adjusting an intensity of the constant current output from the current converter using variable resistance, and an output unit for applying the current received from the current converter to the electrode unit.

Preferably, the signal processing unit includes a buffer for maintaining input impedance higher than skin resistance and for temporarily storing the response signals, a potential difference measurer for measuring a potential difference between the measurement electrodes using the response signals and for outputting a potential difference signal, an offset voltage controller for performing a zero (0) adjustment for the impedance measurement system and for adjusting a direct current (DC) level of the potential difference signal received from the potential difference measurer to shift a measuring range, an amplifier for amplifying the potential difference signal output from the offset voltage controller up to a predetermined level, a filter for removing noise from the amplified potential difference signal, and a phase inverter amplifier for amplifying the noise-filtered potential difference signal and for inverting a phase of the potential difference signal.

Preferably, the image display unit includes a data analyzer for performing a predetermined operation on the potential difference signal received from the signal conversion unit and for outputting analyzed data, an operation controller for determining an operation to be performed by the data analyzer, and a display unit for converting the analyzed data into an image signal and for outputting the image signal.

Preferably, the display unit includes a monitor driver module for converting the potential difference signal into a desired image signal, and an image display device for displaying the image signal.

BRIEF DESCRIPTION OF THE DRAWINGS

The above and other features and advantages of the present invention will become more apparent to those of ordinary skill in the art by describing in detail preferred embodiments thereof with reference to the attached drawings in which.

DETAILED DESCRIPTION OF THE INVENTION

Korean Patent Application No. 2002-43926, filed on Jul. 25, 2002, and entitled: "Measurement System and Electrode for Measuring Skin Impedance in a Small Region of Skin," is incorporated by reference herein in its entirety.

The present invention will now be described more fully hereinafter with reference to the accompanying drawings, in which preferred embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

An impedance measurement electrode according to an embodiment of the present invention includes two current supply electrodes, which are connected to a current source and apply a predetermined current to a small region of the skin, and two measurement electrodes, which measure the reaction of the skin, i.e., a potential difference between the two measurement electrodes contacting the skin, occurring when the predetermined current is applied to the skin. It is preferable that the measurement electrodes are made by processing brass to have a thickness of about 0.8 mm and plating the processed brass with AgCl under the condition of about 100 mA*s/cm². Preferably, a distance between the measurement electrodes is less than about 5 mm.

An impedance measurement electrode according to an embodiment of the present invention includes four electrode rods to implement a four-electrode measurement and is primarily divided into three types, i.e., a circular type, a back and forth type, and a straight-line type, as shown in FIGS. 1A through 1D, FIGS. 2A through 2D, and FIGS. 3A through 3D, respectively. However, it is apparent that other types of four electrodes can be used and that the present invention is not limited to only the types shown.

Figure 1A:
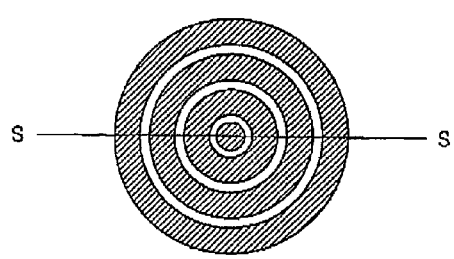
FIGS. 1A through 1D illustrate a circular impedance measurement electrode according to a first preferred embodiment of the present invention.

FIGS. 1A through 1D illustrate a circular impedance measurement electrode according a first preferred embodiment of the present invention. As shown in FIG. 1A, the circular impedance measurement electrode includes a central electrode having a cylindrical structure and three electrodes having a cylindrical structure that surround and are concentrically with the central electrode.

Figure 1B:
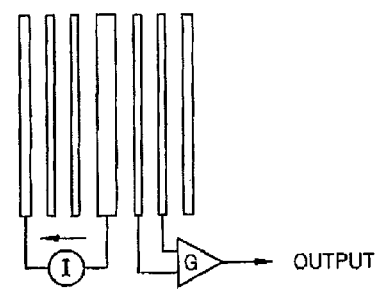

FIG. 1B illustrates a cross-section of the circular impedance measurement electrode taken along the line S-S of FIG. 1A. In FIG. 1B, a current source I is connected to the central electrode and the outermost electrode. Reference character G represents a predetermined gain of operational amplifiers. The other electrodes, between the central electrode and the outermost electrode, are measurement electrodes.

Figure 1C:
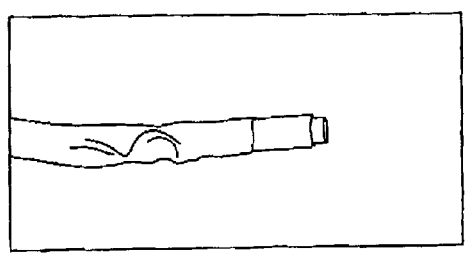
Figure 1D:
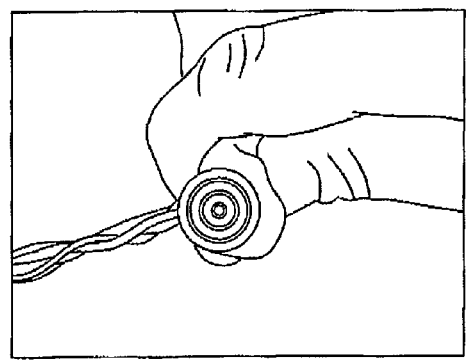

FIGS. 1C and 1D show the appearance and the cross-section, respectively, of an actual circular impedance measurement electrode according to the first preferred embodiment of the present invention.

Figure 2A:
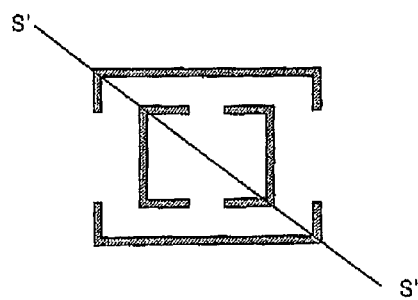
FIGS. 2A through 2D illustrate a back and forth impedance measurement electrode according to a second preferred embodiment of the present invention.

FIGS. 2A through 2D illustrate a back and forth impedance measurement electrode according to a second preferred embodiment of the present invention. Referring to FIG. 2A, the back and forth impedance measurement electrode includes four electrodes. Each of the four electrodes has a structure including a first side, a second side perpendicular to the first side, and a third side, which is perpendicular to the second side and faces the first side. More particularly, each electrode is shaped as a square bracket "[". Hereafter, this structure is referred to as a back-and-forth structure. As shown in FIG. 2A, a first electrode is disposed at a predetermined position, and a second electrode is disposed such that an opening side of the second-17-electrode faces an opening side of the first electrode. Third and fourth electrodes, which are smaller than the first and second electrodes, are disposed within a space defined between the first and second electrodes such that opening side of the respective third and fourth electrodes face each other. Here, the openings of the first and second electrodes are perpendicular to the openings of the third and fourth electrodes. That is, a normal line of the opening portion of each current supply electrode is perpendicular to a normal line of the opening portion of each measurement electrode.

Figure 2B:
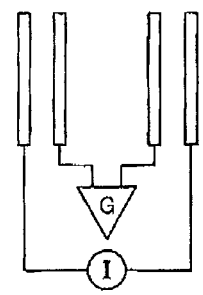
Figure 2C:
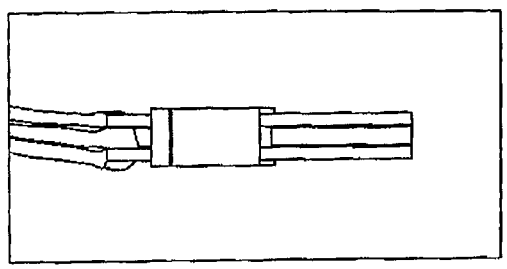
Figure 2D:
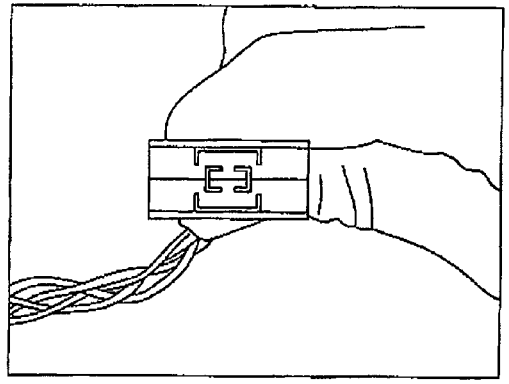

FIG. 2B illustrates a cross-section of the back-and-forth impedance measurement electrode shown in FIG. 2A taken along the line S'-S' of FIG. 2A. In FIG. 2B, a current source I is connected to the first and second electrodes disposed in an outer portion, and the third and fourth electrodes disposed in an inner portion are measurement electrodes. FIGS. 2C and 2D show the appearance and the cross-section, respectively, of an actual back-and-forth impedance measurement electrode according to the second preferred embodiment of the present invention.

In the above embodiment, the electrodes have a back-and-forth structure. However, it will be understood by those skilled in the art that the electrodes may have an oval structure with a predetermined curvature and an opening portion as long as the electrodes are disposed in the same manner as described above. More particularly, each electrode may be shaped as a letter "C".

Figure 3A:
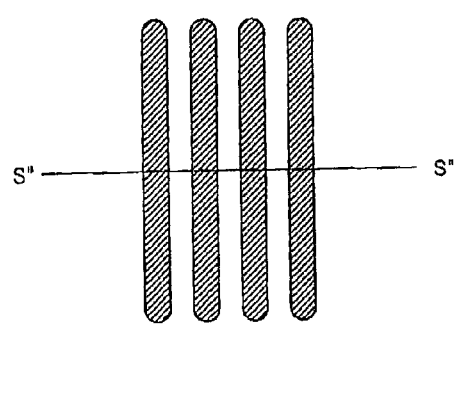
FIGS. 3A through 3D illustrate a straight-line impedance measurement electrode according to a third preferred embodiment of the present invention.
Figure 3B:
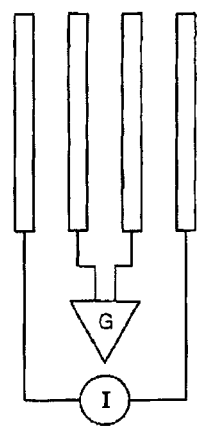
Figure 3C:
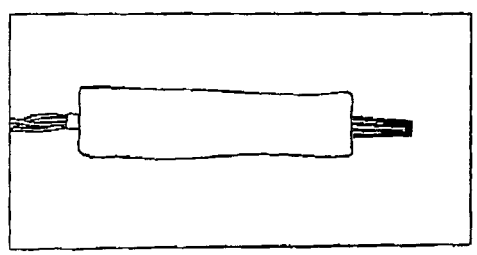
Figure 3D:
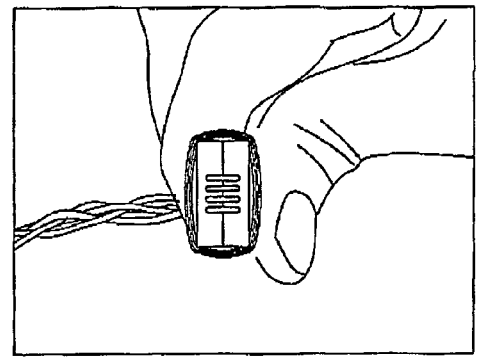

FIGS. 3A through 3D illustrate a straight-line impedance measurement electrode according to a third preferred embodiment of the present invention. As shown in FIG. 3A, in the straight-line shaped impedance measurement electrode, four flat electrodes are disposed in parallel. FIG. 3B illustrates a cross-section of the straight-line impedance measurement electrode shown in FIG. 3A, taken along the line S"-S". In FIG. 3B, a current source I is connected to two outer electrodes, and two inner electrodes are measurement electrodes. FIGS. 3C and 3D show the appearance and the cross-section, respectively, of an actual straight-line impedance measurement electrode according to the third preferred embodiment of the present invention.

Figure 4A:
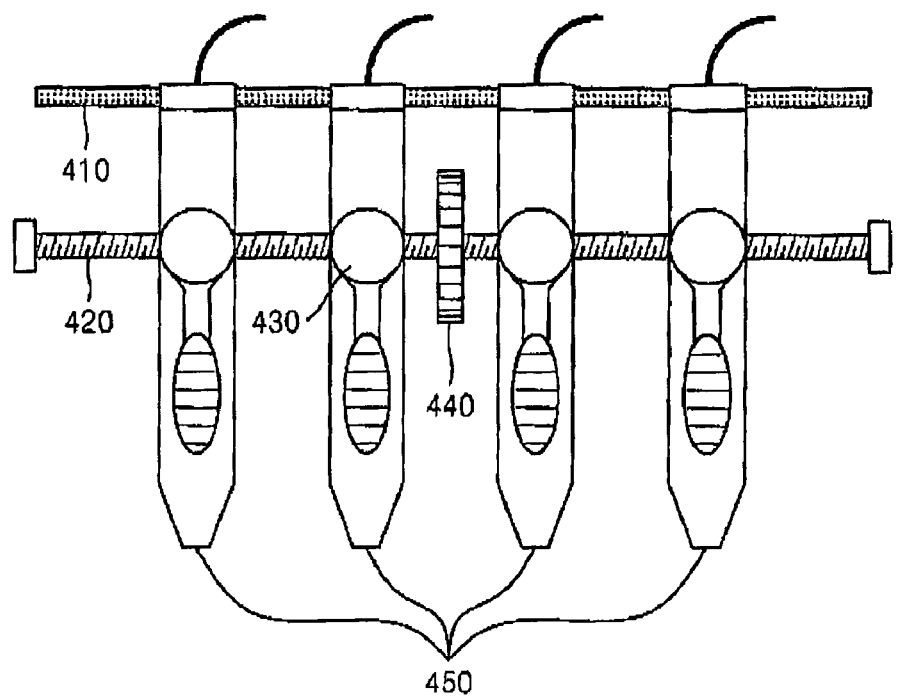
FIGS. 4A and 4B illustrate an electrode distance adjuster according to a preferred embodiment of the present invention.
Figure 4B:
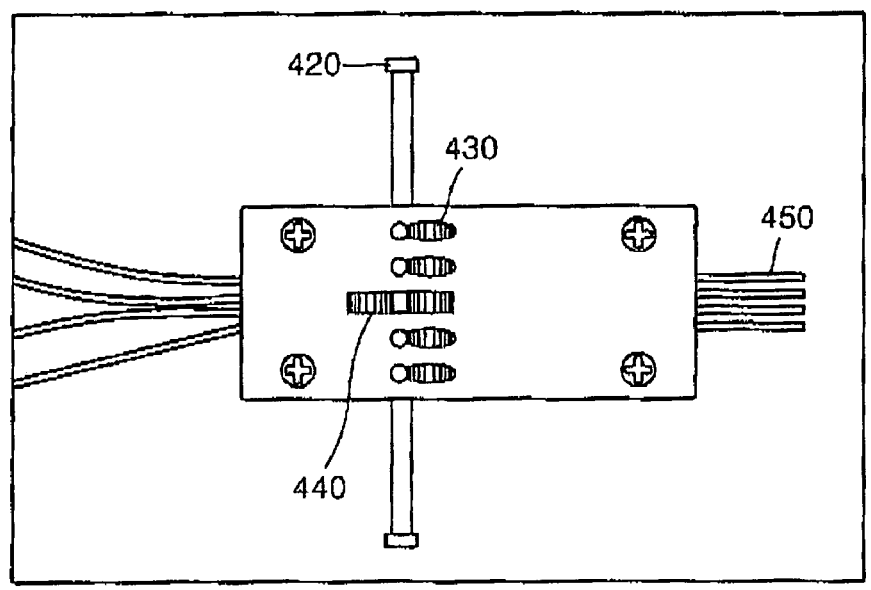

FIGS. 4A and 4B illustrate an electrode distance adjuster according to a preferred embodiment of the present invention. In an embodiment of the present invention, the electrode distance adjuster shown in FIGS. 4A and 4B is combined with an impedance measurement electrode to facilitate adjustment of a distance between electrodes. Since the distance between electrodes, i.e., a skin range in which impedance is measured, can be adjusted to be a relatively small distance, skin impedance may be measured only in a desired small region.

Referring to FIG. 4A, the electrode distance adjuster includes a support bar 410, a stationary screw line 420, fixing studs 430, a rotary screw 440, and electrodes 450. The electrode distance adjuster operates according to a screw method. In operation, the fixing stud 430 for each electrode 450 not to be moved is pushed to fix the corresponding electrode 450. The fixing stud 430 for the electrode 450 that is to be moved is not pushed. Thereafter, when the rotary screw 440 is rotated, the electrode 450 for which the fixing stud 430 is not pushed moves along the stationary screw line 420. In such way, each of the four electrodes 450 is moved by a desired distance in a desired direction, thereby permitting the free adjustment of a distance between the electrodes 450.

FIGS. 4A and 4B show an exemplary electrode distance adjuster for use in combination with the straight-line impedance measurement electrode shown in FIGS. 3A through 3D. However, the electrode distance adjuster can also be applied to the back-and-forth impedance measurement electrode shown in FIGS. 2A through 2D or an impedance measurement electrode having an oval structure with an opening portion. In this case, a first stationary screw line and a first rotary screw for adjusting a distance between inner measurement electrodes and a second stationary screw line and a second rotary screw for adjusting a distance between outer electrodes connected to a current source need to be separately provided.

Figure 7:
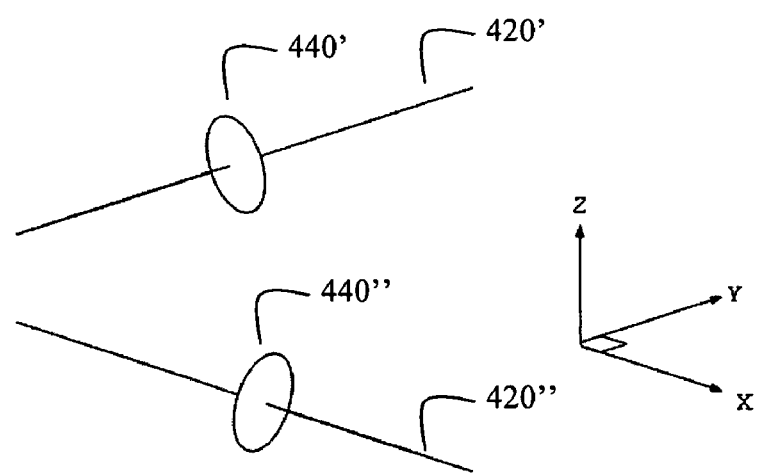
FIG. 7 illustrates a diagram of first and second electrode distance adjusters according to a preferred embodiment of the present invention.

FIG. 7 illustrates a diagram of first and second electrode distance adjusters according to a preferred embodiment of the present invention. Referring to FIG. 7, the first electrode distance adjuster may include a first stationary screw line 420' and a first rotary screw 440' joined to the first stationary screw line 420' and for rotating the first stationary screw line 420'. The second electrode distance adjuster may include a second stationary screw line 420" and a second rotary screw 440" joined to the second stationary screw line 420" and for rotating the second stationary screw line 420". The first stationary screw line 420' and the second stationary screw line 420" may be separated from each other by a predetermined distance and may be perpendicular to each other.

The following description is related to an impedance measurement system for measuring skin impedance in a small region using the above-described four electrodes.

Figure 5A:
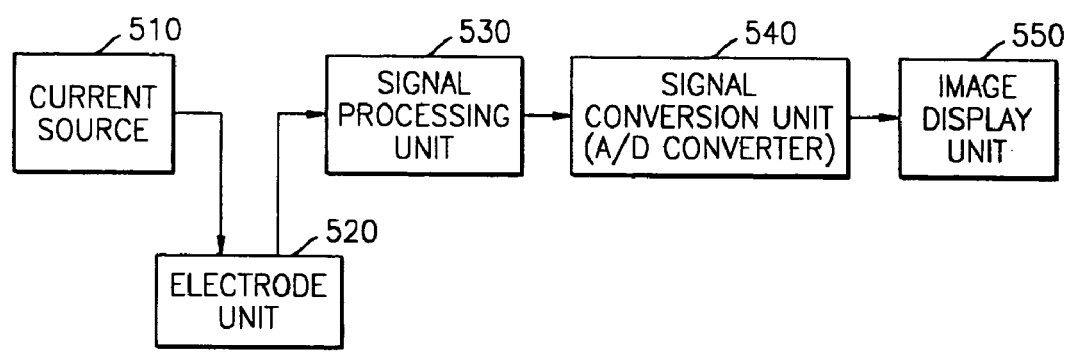
FIGS. 5A through 5D are block diagrams showing an impedance measurement system according to a preferred embodiment of the present invention.

FIGS. 5A through 5D are block diagrams showing an impedance measurement system according to a preferred embodiment of the present invention. Referring to FIG. 5A, the impedance measurement system includes a current source 510, an electrode unit 520, a signal processing unit 530, a signal conversion unit 540, i.e., an analog-to-digital (A/D) converter, and an image display unit 550. The current source 510 supplies a constant current to a small region of the skin in which impedance is to be measured. The electrode unit 520 includes two current supply electrodes that contact the skin and are connected to the current source 510, and two measurement electrodes that contact the skin and are connected to the signal processing unit 530. The signal processing unit 530 receives a signal from each of the measurement electrodes, measures a potential difference between the two measurement electrodes, adjusts a measuring range, removes noise from a potential difference signal, and amplifies the noise-removed potential difference signal. The signal conversion unit 540 converts the analog potential difference signal received from the signal processing unit 530 into a digital potential difference signal. The image display unit 550 analyzes the digital potential difference signal received from the signal conversion unit 540 and outputs data obtained as the result of the analysis.

Figure 5B:
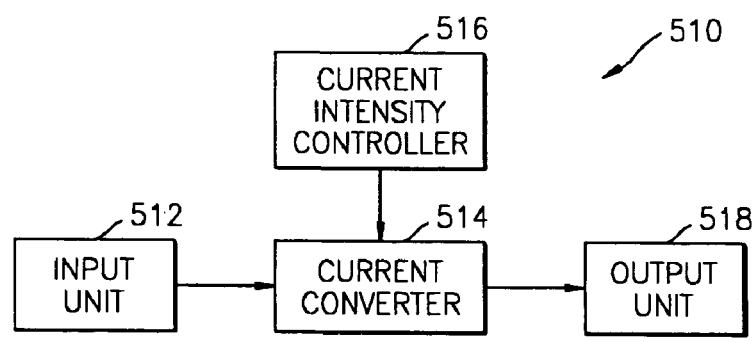

Referring to FIG. 5B, the current source 510, which supplies a constant current regardless of a load in order to give an electrical stimulation to a human skin, includes an input unit 512, a current converter 514, a current intensity controller 516, and an output unit 518.

The input unit 512 receives a voltage from an external power supply unit and divides the received voltage into voltages having a magnitude that can be processed by the current converter 514. The current converter 514 is implemented by a plurality of operational amplifiers. The input unit 512 divides the voltage received from the external power supply unit into voltage units that are supported by each of the operational amplifiers.

The current converter 514 converts a voltage received from the input unit 512 into a constant current using the plurality of operational amplifiers regardless of a load. This conversion is implemented using the characteristics of an operational amplifier and a negative feedback effect.

The current intensity controller 516 controls the intensity of a current to be applied to a load when the current converter 514 converts the voltage into the constant current. This control is implemented by adjusting a ratio, at which the voltage is converted into the constant current, using a variable resistance.

The output unit 518 applies the converted current to a load, i.e., applies the converted current to electrodes of the electrode unit 520, according to a bipolar method. One of the electrodes to which the converted current is applied is connected to a ground of the power supply unit. The output unit 518 applies the current received from the current converter 514 to the electrode unit 520, and, more particularly, to the current supply electrodes of the electrode unit 520. The current is applied to the skin through the current supply electrodes contacting the skin. The measurement electrodes of the electrode unit 520 receive an electrical signal generated in the skin in response to the applied current and output the received signal to the signal processing unit 530.

Figure 5C:
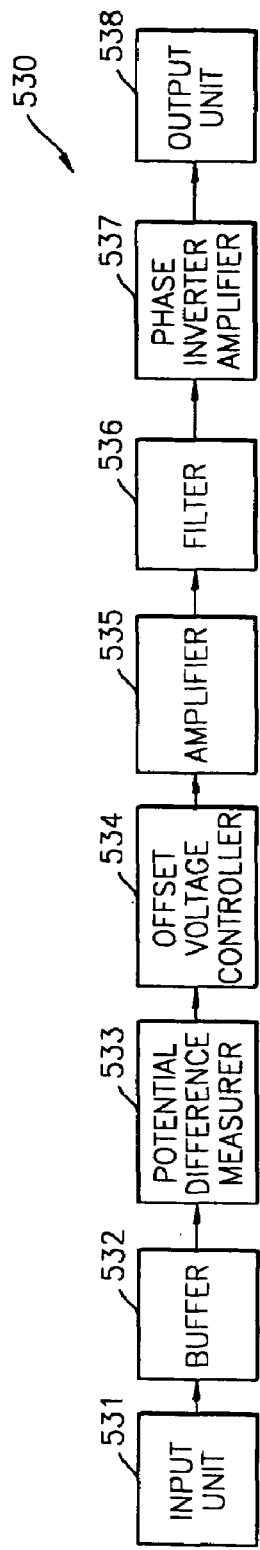

Referring to FIG. 5C, the signal processing unit 530 includes an input unit 531, a buffer 532, a potential difference measurer 533, an offset voltage controller 534, an amplifier 535, a filter 536, a phase inverter amplifier 537, and an output unit 538. The signal processing unit 530 measures response signals generated in the skin in reaction to the current applied to the skin and generates and amplifies a potential difference signal. The human body is a very non-homogeneous medium having a low conductivity, for which it is very difficult to estimate an output value corresponding to an input value. In addition, the level of the response signals is similar to a noise level, that is, a Signal-to-Noise Ratio (SNR) is very low. In this situation, the signal processing unit 530 serves to minimize the influence of a load and noise.

More specifically, the input unit 531 includes a wire having a satisfactory conductivity and electromagnetic shielding effect. The input unit 531 receives the response signals of the skin from the measurement electrodes and outputs the response signals to the buffer 532.

In order to minimize a load effect, in which accurate measurement is difficult when the load of the skin is greater than or similar to an input impedance, the buffer 532 adjusts the input impedance to maintain the input impedance higher than the impedance of the load and temporarily stores the received response signals.

The potential difference measurer 533 receives the response signals, which are respectively detected by the two measurement electrodes, through the buffer 532, measures a potential difference between the two response signals, and outputs a potential difference signal to the offset voltage controller 534.

The offset voltage controller 534 adjusts the voltage level of the impedance measurement system. It is expected that when the two measurement electrodes are in contact with each other before a skin impedance is measured, a potential difference between the two measurement electrodes is zero (0). However, it may happen that the potential difference is non-zero due to an internal factor of the system. In this case, the offset voltage controller 534 adjusts the measured potential difference to zero (0). When signal measurement is performed after zero (0) adjustment, the accurate direct current (DC) level of a measured signal can be measured.

In addition, when the potential difference signal received from the potential difference measurer 533 exceeds a range of a measurable potential range of the impedance measurement system or has an extreme value, the offset voltage controller 534 adjusts the received potential difference signal to within the measurable potential range by adjusting an offset voltage, so that a potential difference can be accurately measured. Moreover, when a user is interested in a minute alternating current (AC) level loaded on the DC level, the user can shift a measuring range to magnify and view only a signal in a domain of interest by adjusting the offset voltage using the offset voltage controller 534.

The amplifier 535 receives the level-adjusted potential difference signal from the offset voltage controller 534 and amplifies it up to an appropriate level using variable resistance. A minute displacement of a signal of interest can be measured by adjusting the degree of amplification using the variable resistance.

The filter 536 receives the amplified potential difference signal from the amplifier 535, removes noise from the potential difference signal, and selectively outputs only the potential difference signal in a desired frequency bandwidth. The filter 536 is implemented as a bandpass filter using a plurality of operational amplifiers and a phase detector circuit. The filter 536 may be implemented as a high-pass or low-pass filter depending on a frequency bandwidth of a signal to be measured. Since the influence of noise is minimized, the potential difference signal output from the filter 536 has a high SNR.

The phase inverter amplifier 537 receives and amplifies the filtered potential difference signal, thereby improving the SNR of the potential difference signal. Thereafter, the phase inverter amplifier 537 inverts the phase of the potential difference signal, which has an inverted phase through the filtering and the amplification, to output the potential difference signal having the same phase as the original potential difference signal to the signal conversion unit 540 through the output unit 538. Here, the output unit 538 adjusts output impedance to be sufficiently small to efficiently transmit the potential difference signal to the signal conversion unit 540.

The signal conversion unit 540 converts the received potential difference signal from an analog format into a digital format so that the potential difference signal can be shown on an image display device, such as a monitor, by the image display unit 550. The digital potential difference signal is output to the image display unit 550.

Figure 5D:
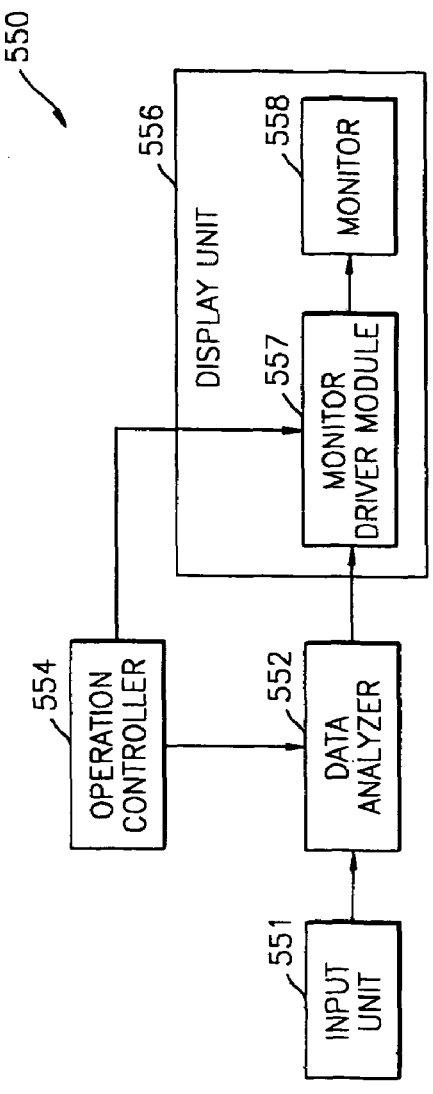

Referring to FIG. 5D, the image display unit 550 includes an input unit 551, a data analyzer 552, an operation controller 554, and a display unit 556, which includes a monitor driver module 557 and an image display device 558, such as a monitor.

The digital potential difference signal output from the signal conversion unit 540 is input to the data analyzer 552 through the input unit 551. The data analyzer 552 performs various operations on the digital potential difference signal so that a user can conveniently use the measured data. Various operations such as averaging, calculating a gradient, differentiating, and integrating can be selectively performed on the potential difference signal during a predetermined period of time as required by a particular application. An operation to be performed is input to the operation controller 554 by the user, and the operation controller 554 determines the operation to be performed.

The analyzed data obtained by performing a predetermined operation on the potential difference signal is transmitted to the display unit 556, then converted into a desired image signal by the monitor driver module 557, and then displayed to the user through the image display device 558, such as a monitor.

Figure 6A:
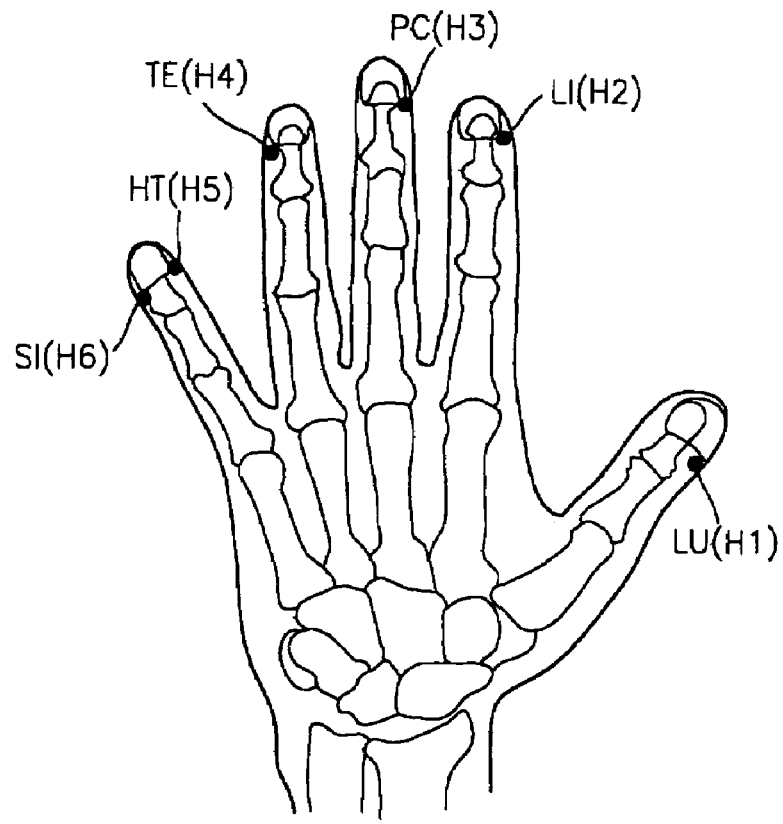
FIGS. 6A and 6B illustrate diagrams showing the positions of meridian points at which skin impedance may be measured using an impedance measurement system according to the present invention.
Figure 6B:
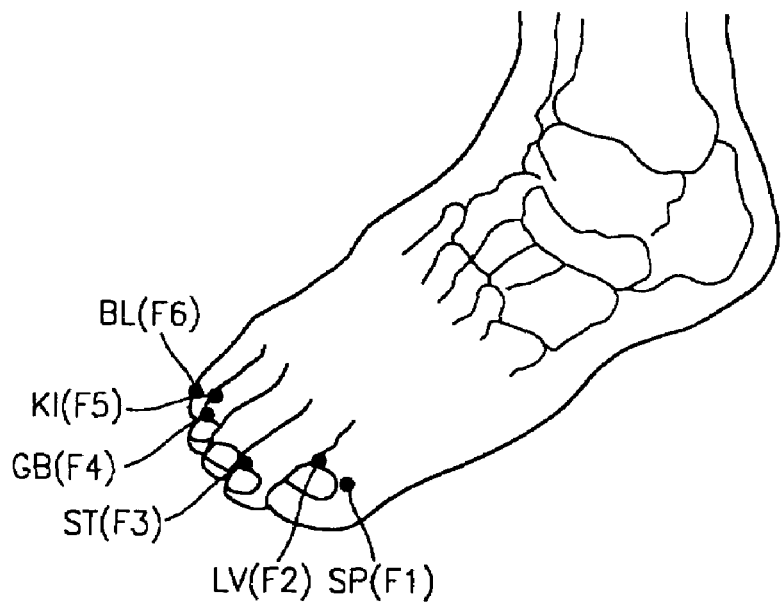

FIGS. 6A and 6B illustrate diagrams showing the positions of various meridian points at which skin impedance may be measured using an impedance measurement system according to an embodiment of the present invention. FIG. 6A shows a lung meridian point LU(H1), a large intestine meridian point LI(H2), a pericardium meridian point PC(H3), a triple energizer meridian point TE(H4), a heart meridian point HT(H5), and a small intestine meridian point SI(H6) on the hand. FIG. 6B shows a spleen meridian point SP(F1), a liver meridian point LV(F2), a stomach meridian point ST(F3), a gallbladder meridian point GB(F4), a kidney meridian point KI(F5), and a bladder meridian point BL(F6) on the foot.

The following table shows the results of exemplary measurements performed using an impedance measurement system according to an embodiment of the present invention.

| Hand | | Foot | |
| --- | --- | --- | --- |
| Measuring points | Skin resistance (100 kΩ) | Measuring points | Skin resistance (100 kΩ) |
| LU(H1) | 1.53 ± 0.86 | SP(F1) | 1.37 ± 0.84 |
| LI(H2) | 1.42 ± 0.87 | LV(F2) | 1.55 ± 0.95 |
| PC(H3) | 1.35 ± 0.86 | ST(F3) | 1.35 ± 0.92 |
| TE(H4) | 1.33 ± 0.85 | GB(F4) | 1.49 ± 0.01 |
| HT(H5) | 1.41 ± 0.88 | KI(F5) | 1.58 ± 0.02 |
| SI(H6) | 1.61 + 0.93 | BL(F6) | 1.53 ± 0.86 |

Here, the skin resistance is equal to an average ± standard deviation.

As shown in the above table, the skin resistance measured on the hand has a regular difference depending on a meridian system ($x^2$=42.67, df=5, P<0.001). The point SI shows the largest resistance characteristic, and the resistance characteristics of the remaining points decrease in the order of LU-LI-HT-PC-TE. The skin resistance measured on the foot also has a regular difference depending on a meridian system ($x^2$=18.06, df=5, P<0.01). The point KI shows the largest resistance characteristic, and the resistance characteristics of the remaining points decrease in order of LV-BL-GB-SP-ST.

The results of the measurement using four electrodes according to an embodiment of the present invention are remarkably different from those obtained via conventional measurements using only two or three electrodes. In addition, it is difficult to simply compare the results of a measurement at the same measuring points if measurement methods are different. A measurement using four electrodes is unique characteristic feature of the present invention.

As described above, unlike conventional two-electrode and three-electrode methods used to measure a composition ratio in the whole body, an impedance measurement system according to the present invention uses an impedance measurement electrode including four electrodes, in which an electrode for supplying a constant current to the skin is separated from a measurement electrode. According to the present invention, measurement electrodes can be concentrated in a small region of the skin so that a skin impedance of a small region can be accurately measured. In addition, the present invention provides an electrode distance adjuster for the four electrodes so that a region of the skin to be measured is freely adjusted.

Preferred embodiments of the present invention have been disclosed herein and, although specific terms are employed, they are used and are to be interpreted in a generic and descriptive sense only and not for purpose of limitation.

Accordingly, it will be understood by those of ordinary skill in the art that various changes in form and details may be made without departing from the spirit and scope of the present invention as set forth in the following claims.

What is claimed is:

1. An impedance measurement system for measuring skin impedance in a small skin region, comprising:
   an electrode unit having a plurality of current supply electrodes for supplying a constant current and a plurality of measurement electrodes separate from the current supply electrodes for measuring a response signal of skin, a first electrode distance adjuster for adjusting a distance between the current supply electrodes, and a second electrode distance adjuster for adjusting a distance between the measurement electrodes, wherein:
      the first electrode distance adjuster includes a first stationary screw line connected to the current supply electrodes, a first rotary screw joined to the first stationary screw line and rotating the first stationary screw line to move the current supply electrodes along the first stationary screw line, and a separate fixing stud for fixing each of the current supply electrodes to the first stationary screw line,
      the second electrode distance adjuster includes a second stationary screw line connected to the measurement electrodes, a second rotary screw joined to the second stationary screw line and rotating the second stationary screw line to move the measurement electrodes along the second stationary screw line, and a separate fixing stud for fixing each of the measurement electrodes to the second stationary screw line, and
      the first stationary screw line and the second stationary screw line are separated from each other by a predetermined distance and are perpendicular to each other; and
   a current source for supplying the constant current to the current supply electrodes,
   wherein the skin impedance is obtained from the measured response signal.

2. The impedance measurement system as claimed in claim 1, wherein the current source comprises:
   an input unit for dividing a voltage received from an external power supply unit into predetermined voltages and for outputting the predetermined voltages;
   a current converter for converting each of the predetermined voltages into a constant current regardless of a load;
   a current intensity controller for adjusting an intensity of the constant current output from the current converter using variable resistance; and
   an output unit for applying the current received from the current converter to the electrode unit.

3. The impedance measurement system as claimed in claim 1, further comprising an image display unit including:
   a data analyzer for performing a predetermined operation on a potential difference signal received from a signal conversion unit and for outputting analyzed data;
   an operation controller for determining an operation to be performed by the data analyzer; and
   a display unit for converting the analyzed data into an image signal and for outputting the image signal.

4. The impedance measurement system as claimed in claim 1, wherein the measurement electrodes are disposed between the current supply electrodes.

5. The impedance measurement system as claimed in claim 4, wherein the plurality of current supply electrodes comprises a first electrode and a second electrode, opposite the first electrode, and wherein the plurality of measurement electrodes are in a space defined between the first and second electrodes.

6. The impedance measurement system as claimed in claim 5, wherein at least one of the first electrode, the second electrode and the plurality of measurement electrodes has an open two dimensional shape.

7. The impedance measurement system as claimed in claim 6, wherein the measurement electrodes are disposed perpendicular to the first and second electrodes.

8. The impedance measurement system as claimed in claim 6, wherein the first and second electrodes have complementary open two dimensional shapes.

9. The impedance measurement system as claimed in claim 8, wherein the first electrode has a first side, a second side perpendicular to the first side, and a third side perpendicular to the second side and facing the first side; and
   the second electrode has a same shape as the first electrode, the second electrode being disposed separate from the first electrode such that an opening side of the second electrode faces an opening side of the first electrode.

10. The impedance measurement system as claimed in claim 8, wherein the measurement electrodes are disposed perpendicular to the first and second electrodes.

11. The impedance measurement system as claimed in claim 8, wherein the first electrode has an oval structure with an opening portion and a predetermined curvature; and
   the second electrode has a same shape as the first electrode, the second electrode being disposed separate from the first electrode such that an opening of the second electrode faces an opening of the first electrode.

12. The impedance measurement system as claimed in claim 8, wherein the plurality of measurement electrodes comprise third and fourth electrodes having complementary open two dimensional shapes.

13. The impedance measurement system as claimed in claim 12, wherein the first, second, third and fourth electrodes have a same open two dimensional shape.

14. The impedance measurement system as claimed in claim 13, wherein the third and fourth electrodes are disposed perpendicular to the plurality of current supply electrodes.

15. The impedance measurement system as claimed in claim 6, wherein the plurality of measurement electrodes comprise third and fourth electrodes having complementary open two dimensional shapes.

16. The impedance measurement system as claimed in claim 15, wherein the third electrode has a first side, a second side perpendicular to the first side, and a third side perpendicular to the second side and facing the first side; and
   the fourth electrode has a same shape as the third electrode, the fourth electrode being disposed separate from the third electrode such that an opening side of the fourth electrode faces an opening side of the third electrode.

17. The impedance measurement system as claimed in claim 15, wherein the third and fourth electrodes are disposed perpendicular to the plurality of current supply electrodes.

18. The impedance measurement system as claimed in claim 15, wherein the third electrode has an oval structure with an opening portion and a predetermined curvature; and
   a fourth electrode has a same shape as the third electrode, the fourth electrode being disposed separate from the third electrode such that an opening of the fourth electrode faces an opening of the third electrode.

19. The impedance measurement system as claimed in claim 1, further comprising a signal processing unit, which is connected to the measurement electrodes, for receiving response signals generated in the skin in response to the applied constant current, for generating a potential difference signal, for removing noise from the potential difference signal, and for amplifying the noise-removed potential difference signal.

20. The impedance measurement system as claimed in claim 19, wherein the signal processing unit comprises:
   a buffer for maintaining an input impedance higher than a skin resistance and for temporarily storing the response signals;
   a potential difference measurer for measuring a potential difference between the measurement electrodes using the response signals and for outputting a potential difference signal;
   an offset voltage controller for performing a zero adjustment for the impedance measurement system and for adjusting a direct current level of the potential difference signal received from the potential difference measurer to shift a measuring range;
   an amplifier for amplifying the potential difference signal output from the offset voltage controller up to a predetermined level;
   a filter for removing noise from the amplified potential difference signal; and
   a phase inverter amplifier for amplifying the noise-filtered potential difference signal and for inverting a phase of the noise-filtered potential difference signal.

21. The impedance measuring system as claimed in claim 1, wherein the measured response signal is a direct current signal.

22. An impedance measurement electrode used to measure skin impedance in a small skin region, comprising:
   a plurality of current supply electrodes for supplying a constant current to skin;
   a plurality of measurement electrodes, which are separated from the current supply electrodes, for measuring a response signal of the skin;
   a first electrode distance adjuster for adjusting a distance between the current supply electrodes; and
   a second electrode distance adjuster for adjusting a distance between the measurement electrodes, wherein:
      the first electrode distance adjuster includes a first stationary screw line connected to the current supply electrodes, a first rotary screw joined to the first stationary screw line and rotating the first stationary screw line to move the current supply electrodes along the first stationary screw line, and a separate fixing stud for fixing each of the current supply electrodes to the first stationary screw line,
      the second electrode distance adjuster includes a second stationary screw line connected to the measurement electrodes, a second rotary screw joined to the second stationary screw line and rotating the second stationary screw line to move the measurement electrodes along the second stationary screw line, and a separate fixing stud for fixing each of the measurement electrodes to the second stationary screw line, and
      the first stationary screw line and the second stationary screw line are separated from each other by a predetermined distance and are perpendicular to each other.

23. The impedance measurement electrode as claimed in claim 22, wherein the measurement electrodes have a thickness of about 0.8 mm.

24. The impedance measurement electrode as claimed in claim 22, wherein a distance between the measurement electrodes is less than about 5 mm.

25. The impedance measurement electrode as claimed in claim 22, wherein the measuring electrodes are disposed between the current supply electrodes.

26. The impedance measurement electrode as claimed in claim 25, wherein the measurement electrodes are disposed perpendicular to the current supply electrodes.

27. The impedance measurement electrode as claimed in claim 25, wherein the plurality of current supply electrodes comprises a first electrode and a second electrode, opposite the first electrode, and wherein the plurality of measurement electrodes are in a space defined between the first and second electrodes.

28. The impedance measurement electrode as claimed in claim 27, wherein at least one of the first electrode, the second electrode and the plurality of measurement electrodes has an open two dimensional shape.

29. The impedance measurement electrode as claimed in claim 28, wherein the first and second electrodes have complementary open two dimensional shapes.

30. The impedance measurement electrode as claimed in claim 29, the first electrode has a first side, a second side perpendicular to the first side, and a third side perpendicular to the second side and facing the first side; and
   the second electrode has a same shape as the first electrode, the second electrode being disposed separate from the first electrode such that an opening of the second electrode faces an opening of the first electrode.

31. The impedance measurement electrode as claimed in claim 29, wherein the measurement electrodes are disposed perpendicular to the first and second electrodes.

32. The impedance measurement electrode as claimed in claim 29, wherein the first electrode has an oval structure with an opening portion and a predetermined curvature; and
   the second electrode has a same shape as the first electrode, the second electrode being disposed separate from the first electrode such that an opening of the second electrode faces an opening of the first electrode.

33. The impedance measurement electrode as claimed in claim 29, wherein the plurality of measurement electrodes comprise third and fourth electrodes having complementary open two dimensional shapes.

34. The impedance measurement electrode as claimed in claim 33, wherein the third and fourth electrodes are disposed perpendicular to the plurality of current supply electrodes.

35. The impedance measurement electrode as claimed in claim 33, wherein a normal line of an open portion of each current supply electrode is perpendicular to a normal line of an open portion of each measurement electrode.

36. The impedance measurement electrode as claimed in claim 33, wherein the first, second, third and fourth electrodes have a same open two dimensional shape.

37. The impedance measurement electrode as claimed in claim 36, wherein a normal line of an open portion of each current supply electrode is perpendicular to a normal line of an open portion of each measurement electrode.

38. The impedance measurement electrode as claimed in claim 28, wherein the plurality of measurement electrodes comprise third and fourth electrodes having complementary open two dimensional shapes.

39. The impedance measurement electrode as claimed in claim 38, wherein the third electrode has a first side, a second side perpendicular to the first side, and a third side perpendicular to the second side and facing the first side; and
   the fourth electrode has a same shape as the third electrode, the fourth electrode being disposed separate from the third electrode such that an opening side of the fourth electrode faces an opening side of the third electrode.

40. The impedance measurement electrode as claimed in claim 38, wherein the third and fourth electrodes are disposed perpendicular to the plurality of current supply electrodes.

41. The impedance measurement electrode as claimed in claim 38, wherein the third electrode has an oval structure with an opening portion and a predetermined curvature; and a fourth electrode has a same shape as the third electrode, the fourth electrode being disposed separate from the third electrode such that an opening of the fourth electrode faces an opening of the third electrode.

* * * * *